United States Patent [19]

Kuo et al.

[11] Patent Number: 4,749,820

[45] Date of Patent: * Jun. 7, 1988

[54] INTEGRATION OF PARAFFIN DEHYDROGENATION WITH MOGD TO MINIMIZE COMPRESSION AND GAS PLANT SEPARATION

[75] Inventors: James C. Kuo, Cherry Hill; Samuel A. Tabak, Wenonah, both of N.J.

[73] Assignee: Mobil Oil Corporation, New York, N.Y.

[*] Notice: The portion of the term of this patent subsequent to Sep. 17, 2002 has been disclaimed.

[21] Appl. No.: 650,594

[22] Filed: Sep. 14, 1984

[51] Int. Cl.[4] ............... C07C 5/00; C07C 1/00
[52] U.S. Cl. ................ 585/330; 585/319; 585/415; 585/413; 585/254; 585/517; 585/533
[58] Field of Search .......... 585/330, 319, 415, 413, 585/254, 654, 517, 533

[56] References Cited

U.S. PATENT DOCUMENTS

| | | | |
|---|---|---|---|
| 3,960,978 | 6/1976 | Givens et al | 260/0.15 R |
| 4,021,502 | 5/1977 | Plank et al. | 260/0.15 R |
| 4,100,218 | 7/1978 | Chen et al. | 260/673 |
| 4,150,062 | 4/1979 | Garwood et al. | 260/673 |
| 4,191,846 | 3/1980 | Farha, Jr. et al. | 585/440 |
| 4,197,185 | 4/1980 | LePage et al. | 208/71 |
| 4,211,640 | 7/1980 | Garwood et al. | 208/255 |
| 4,227,992 | 10/1980 | Garwood et al. | 208/46 |
| 4,374,046 | 2/1983 | Antos | 585/660 |
| 4,381,417 | 4/1984 | Vora et al. | 585/654 |
| 4,413,153 | 11/1983 | Garwood et al. | 585/304 |
| 4,433,185 | 2/1984 | Tabak | 585/312 |
| 4,435,607 | 3/1984 | Imai | 585/654 |
| 4,450,311 | 5/1984 | Wright et al. | 585/413 |
| 4,456,779 | 6/1984 | Owen et al. | 585/413 |
| 4,456,781 | 6/1984 | Marsh et al. | 585/533 |
| 4,497,968 | 2/1985 | Wright et al. | 585/304 |
| 4,517,396 | 5/1985 | Huck et al. | 585/415 |
| 4,542,247 | 9/1985 | Chang et al. | 585/254 |
| 4,675,461 | 6/1987 | Owen et al. | 585/330 |
| 4,678,645 | 7/1987 | Chang et al. | 422/190 |

OTHER PUBLICATIONS

Kirk-Othmer, *Encyclopedia of Chemical Technology*, 3rd Ed, vol. 19, "Powder Coatings to Recycling", pp. 232-235 (Propylene); John Wiley & Sons, 1979.

*Oil & Gas Journal*-Dec. 8, 1980, "Dehydrogenation links LPG to More Octanes" pp. 96-101; S. Gussow et al, Houdry Div., Air Products & Chemicals, Inc., Allentown, Pa.

*Hydrocarbon Processing*, Apr. 1982, "$C_2/C_5$ Dehydrogenation Updated" by B. V. Vora and T. Imai, UOP Inc., Des Plaines, Ill., pp. 171-174.

*Primary Examiner*—Helen M. S. Sneed
*Assistant Examiner*—Chung K. Pak
*Attorney, Agent, or Firm*—Alexander J. McKillop; Michael G. Gilman; L. G. Wise

[57] ABSTRACT

Disclosed is a method and apparatus for producing gasoline and distillate grade products which employs integrating catalytic (or thermal) dehydrogenation of paraffins with MOGD to minimize interstage compression and gas plant separation cost. The process cascades the product from a low temperature propane or butane dehydrogenation zone into a first catalytic reactor zone which operates at low pressure and contains zeolite oligomerization catalysts, where the low molecular weight olefins are reacted to primarily gasoline range materials. These gasoline range materials can then be pressurized to the pressure required for reacting to distillate in a second catalytic reactor zone operating at high pressure and containing zeolite oligomerization catalyst. The first catalytic reactor zone also acts to remove the olefins from the dehydrogenation reactor effluent to allow recycle of the unreacted paraffins.

20 Claims, 2 Drawing Sheets

EFFECT OF OLEFIN PRESSURE ON PRODUCT

INTEGRATION OF PARAFFIN DEHYDROGENATION WITH MOGD TO MINIMIZE COMPRESSION AND GAS PLANT SEPARATION

BACKGROUND OF THE INVENTION

1. Field of the Invention

This invention relates to a method and apparatus for converting paraffins to higher hydrocarbons, such as gasoline range or distillate range fuels. In particular, it relates to methods and apparatus which combine the operation of catalytic dehydrogenation of a paraffinic feedstock to produce olefins with the operation of a multiple-stage catalytic reactor system to convert olefins to gasoline and higher hydrocarbons, and with downstream separation units to optimize heat recovery and product selectivity.

2. Discussion of the Prior Art

The conversion of paraffins, such as propane and butane, to mono-olefins, such as propylene and butylene, has been accomplished by thermal or catalytic dehydrogenation. A general discussion of thermal dehydrogenation (i.e., steam cracking) is presented in *Encyclopedia of Chemical Technology*, Ed. by Kirk and Othmer, Vol. 19, 1982, Third Ed., pp. 232–235. Various processes for catalytic dehydrogenation are available in the prior art. These processes include the Houdry Catofin process of Air Products and Chemicals, Inc., Allentown, Pa., the Oleflex process of UOP, Inc., Des Moines, Ill. and a process disclosed by U.S. Pat. No. 4,191,846. The Houdry Catofin process, described in a magazine article, "Dehydrogenation Links LPG to More Octanes", Gussow et al, *Oil and Gas Journal*, Dec. 8, 1980, involves a fixed bed, multi-reactor catalytic process for conversion of paraffins to olefins. Typically, the Houdry Catofin process runs at low pressures of 5–30 inches of mercury absolute, and high temperatures with hot reactor effluent at 550°–650° C. Dehydrogenation is an endothermic reaction, so it normally requires a furnace to provide heat to a feed stream prior to feeding the feed stream into the reactors. The UOP Oleflex process, disclosed in an article "$C_2/C_5$ Dehydrogenation Updated", Verrow et al, *Hydrocarbon Processing*, April 1982, uses stacked catalytic reactors U.S. Pat. No. 4,191,846 teaches the use of group VIII meta containing catalysts to promote catalytic dehydrogenation of paraffins to olefins.

Recent developments in zeolite catalysts and hydrocarbon conversion methods and apparatus have created interest in utilizing olefinic feedstocks for producing heavier hydrocarbons, such as $C_5+$ gasoline or distillate. These developments have contributed to the development of the Mobil olefins to gasoline/distillate (MOGD) method and apparatus.

In MOGD, olefins are catalytically converted to heavier hydrocarbons by catalytic oligomerization using an acid crystalline zeolite, such as a ZSM-5 type catalyst. Process conditions can be varied to favor the formation of either gasoline or distillate range products. In U.S. Pat. Nos. 3,960,978 and 4,021,502, Plank, Rosinski and Givens disclose conversion of $C_2$–$C_5$ olefins, alone or in combination with paraffinic components, into higher hydrocarbons over a crystalline zeolite catalyst. Garwood et al have also contributed improved processing techniques to the MOGD system, as in U.S. Pat. Nos. 4,150,062; 4,211,640; and 4,227,992. Marsh et al, in U.S. Pat. No. 4,456,781, have also disclosed improved processing techniques for the MOGD system.

The conversion of olefins in a MOGD system may occur in a gasoline mode or a distillate mode. In the gasoline mode, the olefins are catalytically oligomerized at high temperature ranging from 400°–800° F. and moderate pressure ranging from 10–1000 psia. To avoid excessive temperatures in the exothermic reactor, the olefinic feed may be diluted. In the gasoline mode, the diluent may comprise light hydrocarbons, such as $C_3$–$C_4$, from the feedstock and/or recycled from debutanized product. In the distillate mode, olefins are catalytically oligomerized at high temperature ranging from 350°–600° F. and higher pressure ranging from 100–1000 psia than the gasoline mode. In the distillate mode operation, olefinic gasoline may be recycled and futher oligomerized, as disclosed in U.S. Pat. No. 4,211,640 (Garwood and Lee). U.S. Pat. No. 4,433,185 (Tabak) teaches the use of a two-stage catalytic oligomerization system in which a first stage operates in the distillate mode and a second stage operates in the gasoline mode.

Olefinic feedstocks may be obtained from various sources, including from fossil fuel processing streams, such as gas separation units, from the cracking of $C_2+$ hydrocarbons, from coal by-products and from various synthetic fuel processing streams. U.S. Pat. No. 4,100,218 (Chen et al) teaches thermal cracking of ethane to ethlyene, with subsequent conversion of ethylene to LPG and gasoline over a ZSM-5 type zeolite catalyst.

Although heavier hydrocarbons, such as gasoline and distillate, can be produced from propane and butane by the prior art using dehydrogenation integrated with MOGD, there are several problems with integrating these processes, particularly to produce distillate. For example, U.S. Pat. No. 4,413,153 (Garwood et al) discloses a system which catalytically (or themally) dehydrogenates the paraffins to olefins, and then reacts the olefins by catalytic oligomerization (MOGD), to distillate range material. Catalytic oligomerization in the distillate mode is a high (preferably greater than 600 psig) pressure process, whereas dehydrogenation is favored by lower (less than 25 psig) pressure. Also, the dehydrogenation zone effluent is typically in vapor form. As a consequence, a compressor is required for pressurizing the effluent to feed a catalytic oligomerization reactor zone operating in the distillate mode, thus resulting in expensive compression costs. It would be preferable to feed a catalytic oligomerization reactor zone, particularly if operating in the distillate mode, as a liquid. U.S. Pat. No. 4,413,153 (Garwood et al) also provides a liquid feed to a catalytic oligomerization reactor zone by separating the dehydrogenation zone effluent in a separation zone to form a $C_2^-$ gaseous stream and a $C_3+$ liquid stream. Typically, such a separation is accomplished in a refrigerated distillation column. However, it is energy inefficient to feed gases at temperatures greater than 100° F. to a refrigerated distillation column and then heat the $C_3+$ liquid stream produced by distillation to greater than 350° F. prior to feeding to catalytic oligomerization.

Moreover, dehydrogenation produces a dilute olefinic stream comprising 20–50% $C_3/C_4$ olefins and the remainder comprising $C_3/C_4$ paraffins. It is desirable to separate the olefins from the paraffins prior to feeding the olefins to a distillate mode catalytic oligomerization reactor zone. This separation reduces the rate and pressurization requirements of the distillate mode feedstream and facilitates recycle of paraffins to the dehydrogenation zone. At present, expensive gas plant separation is required to separate $C_3/C_4$ olefins from $C_3/C_4$ paraffins.

SUMMARY OF THE INVENTION

The invention minimizes the above noted compression and gas plant problems, while producing heavier hydrocarbons from $C_3/C_4$ paraffins, by intergrating a gasoline mode catalytic oligomerization reactor zone and a dehydrogenation zone. Within the gasoline mode reactor zone, 70-95% of $C_3/C_4$ olefins convert to olefinic gasoline. The effluent from the gasoline mode reactor zone is separated into a $C_4^-$ stream comprising $C_3/C_4$ paraffins and $C_3/C_4$ olefins, which are recycled to the dehydrogenation zone, and a $C_5^+$ rich stream comprising olefinic gasoline. The compression requirements for a feedstream to a catalytic oligomerization reactor zone are reduced because the gasoline mode reactor zone operates at lower pressure than the distillate mode reactor zone. The gas plant costs are reduced because it is relatively easy to separate the $C_5^+$ rich stream, comprising the $C_4^-$ stream, comprising olefinic gasoline, from the $C_3/C_4$ paraffins and $C_3/C_4$ olefins, compared to the difficult separation of $C_3/C_4$ olefins from $C_3/C_4$ paraffins.

The invention minimizes the above noted compression and gas plant problems while producing distillate from $C_3/C_4$ paraffins by inegrating the gasoline mode catalytic oligomerization reactor zone between the dehydrogenation zone and a distillate mode catalytic oligomerization reactor zone. The $C_5^+$ rich stream from the gasoline mode reactor zone feeds the distillate mode reactor zone as a liquid, so it may be pumped to the pressure required and thus eliminates compression. In addition, the separation of $C_3/C_4$ paraffins from the gasoline mode reactor zone effluent, reduces the rate of the feedstream to the distillate mode and, as mentioned above, reduces gas plant costs.

Accordingly, it is a primary object of this invention to provide an improved method and apparatus for converting paraffins to heavier hydrocarbons by integrating dehydrogenation of propane/butane to produce olefins with a low pressure oligomerization of olefins to produce gasoline followed by a higher pressure oligomerization of gasoline to produce gasoline and distillate.

It is another object of this invention to provide an improved method and apparatus for converting propane/butane to gasoline/distillate by integrating dehydrogenation of propane/butane to produce olefins with oligomerization of olefins to produce gasoline and/or distillates.

It is another object of this invention to provide a method and apparatus for converting olefins from a mixed olefin/paraffin stream to gasoline and facilitating recycle of paraffins.

It is another object of this invention to provide a method and apparatus which converts propane/butane to gasoline with reduced gas plant costs.

It is another object of this invention to provide a method and apparatus which integrates dehydrogenation of propane/butane to produce olefins with oligomerization of olefins to produce gasoline and/or distillates, while reducing the need for dehydrogenation plant product compression.

In its method aspects, the invention achieves the foregoing objects by a method for producing heavier hydrocarbons of gasoline or distillate boiling range which comprises the steps of: passing a paraffinic feed stream comprising $C_3/C_4$ into a dehydrogenation zone at conditions of low pressure at about 0.1-2 atms. and high temperature at about 1000°-1700° F., which favor conversion of the paraffinic feed stream to an olefin rich effluent stream comprising propylene or butylene, depending on whether the feed stream is propane rich or butane rich; contacting the olefin rich effluent stream with a crystalline zeolite oligomerization catalyst in a first catalytic reactor zone at conditions of low pressure ranging from 10-1000 psia and high temperature ranging from 400°-800° F., which favor conversion of olefins to a first reactor effluent stream rich in olefinic gasoline range hydrocarbons; and flashing the first reactor effluent stream in a first separation zone to form a first $C_4^-$ rich stream and a $C_5^+$ rich stream. A first portion of the $C_5^+$ rich stream is preferably used as olefinic feedstock to a second catalytic reactor zone where it contacts a crystalline zeolite oligomerization catalyst at high pressure ranging from 100°-2000 psig and high temperature ranging from 350°-600° F. under conditions favorable for production of a second reactor effluent stream rich in distillate. The second reactor effluent stream passes into a second separation zone to recover a second $C_4^-$ rich stream, a gasoline product stream, and a distillate product stream.

The method may include the steps of recycling a portion of the $C_4^-$ rich stream into the dehydrogenation zone and the $C_5^+$ rich stream into the first catalytic reactor zone. The method may also include the steps of heat exchange of the paraffinic feed stream and the olefinic feedstock with various other fluid streams to recover heat.

In its apparatus respects, the invention comprises: means for passing a paraffinic feed stream to a dehydrogenation zone, which converts the paraffinic feed stream to an olefin rich effluent stream; means for passing the olefin rich effluent stream to a first catalytic reactor zone where it contacts with a crystalline zeolite oligomerization catalyst at conditions of low pressure and high temperature to convert a major portion of olefins to olefinic gasoline range hydrocarbons which form a first reactor effluent stream; and means for separating the first reactor effluent stream in a first separation zone to form a first $C_4^-$ rich stream and a $C_5^+$ rich stream. The preferred form of the apparatus further comprises: means for passing a first portion of the $C_5^+$ rich stream as an olefinic feedstock to a second catalytic reactor zone, where the olefinic feedstock contacts a crystalline zeolite oligomerization catalyst at high pressure and high temperature to convert a major portion of the olefinic feedstock to distillate which leaves as a second reactor effluent stream; and means for separating the second reactor effluent stream into a second $C_4^-$ rich stream, a gasoline product stream, and a distillate rich product stream.

The apparatus may include means for recycling a portion of the first $C_4^-$ rich stream, the $C_5^+$ rich stream and the gasoline product stream to the dehydrogenation zone, the first catalytic reactor zone and the second catalytic reactor zone respectively. The apparatus may also include means for heat exchanging the paraffinic feed stream and the olefinic feedstock with various process fluid streams.

DETAILED DESCRIPTION OF THE INVENTION

The novel method of this invention involves the cascading of the product from a low pressure dehydrogenation of low molecular weight paraffins, such as propane and/or butane, into a low pressure catalytic oligomerization reactor, where the olefins produced by dehydrogenation are reacted primarily to olefinic gasoline range materials, which can then be pressurized to the pressure required for reacting to distillate in a high pressure catalytic oligomerization reactor.

Figure 1:
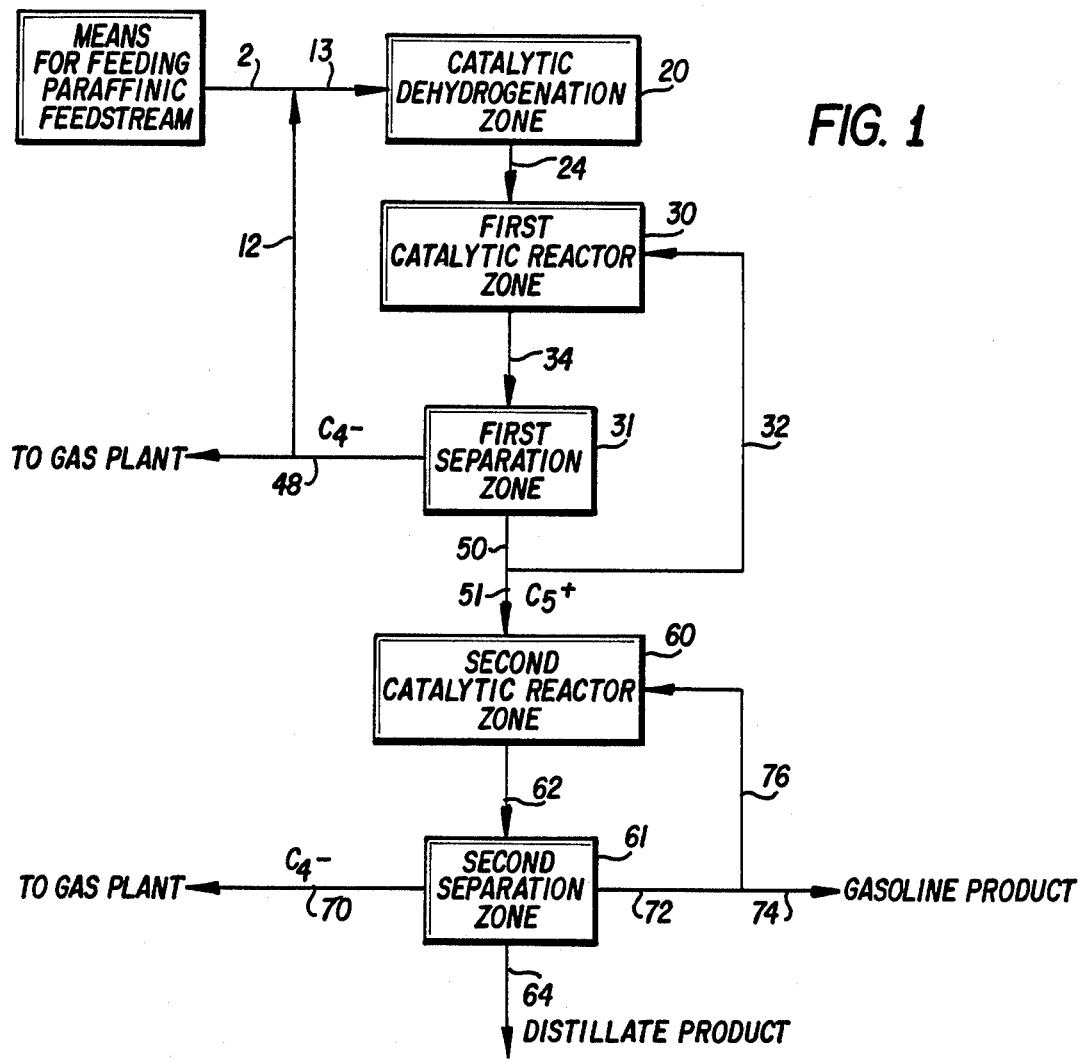
FIG. 1 is a process flow sheet showing the overall method aspects of the invention.

In FIG. 1, the overall method of the invention is shown in flow diagram form. A paraffinic feed stream 2, comprising propane and/or butane, is combined with recycled paraffinic feed stream 12, to form a paraffinic feed stream 13 which passes to a catalytic dehydrogenation zone 20, which operates at low pressure and high temperature (preferred values are discussed below) to convert the combined paraffinic feed stream 13 to an olefin rich effluent stream 24. Although the dehydrogenation zone 20 is preferably catalytic, it can be a thermal dehydrogenation zone instead. Stream 24 passes into a first catalytic reactor zone 30, which operates at low pressure and high temperature (preferred values are discussed below) to convert the olefins to olefinic gasoline which exits in first reactor effluent stream 34. Stream 34 then enters a first separation zone 31 which forms a first $C_4^-$ rich stream 48 and a $C_5^+$ rich stream 50. A portion of the first $C_4^-$ rich stream 48 is recycled to the catalytic dehydrogenation zone 20 as recycle paraffinic feed stream 12. The unrecycled portion of the first $C_4^-$ rich stream 48 is sent to a gas plant for separation into its components such as $H_2$, Fuel Gas and a paraffins feedstock 6, shown in FIG. 2, which may recycle to the catalytic dehydrogenation zone 20. Also, a portion of the $C_5^+$ rich stream 50 may be recycled as recycle stream 32 to the first catalytic reactor zone 30. The unrecycled portion of the $C_5^+$ rich stream 50 is the olefinic feedstock 51, which is passed to a second catalytic reactor zone 60 to convert the olefinic gasoline to distillate. The distillate passes from the second catalytic reactor zone 60 as second reactor effluent stream 62 into a second separation zone 61. The second separation zone 61 separates the seond reactor effluent stream 62 into a second $C_4^-$ rich stream 70 which passes to the gas plant, a distillate product stream 64 and a liquid gasoline stream 72. The liquid gasoline stream 72 may be divided into a gasoline product stream 74 and a gasoline recycle stream 76 which recycles to the second catalytic reactor zone 60. The recycle streams 32,76 are optional, but may be used to dilute the feed to the first and second catalytic reactor zones 30,60, respectively to better control the temperature due to the exothermic nature of the reactions in both catalytic reactor zones.

The process illustrated in FIG. 1 reduces gas plant and compression costs by converting a major portion of the $C_3/C_4$ type olefins produced in the catalytic dehydrogenation zone 20 to olefinic gasoline range materials in the first catalytic reactor zone 30. This reduces gas plant costs by facilitating the separation of olefinic materials from the paraffinic materials in the first separation zone 31, because the olefinic gas range materials are easy to separate from the unreacted paraffins, as compared to the relatively difficult step of separating $C_3/C_4$ type olefins from $C_3/C_4$ type paraffins. Therefore, the paraffinic materials are removed in the first $C_4^-$ rich stream 48, whereas the olefinic materials are mainly removed in the $C_5^+$ rich stream 50. The $C_5^+$ rich stream 50 then enters the second catalytic reactor zone 60 to convert a portion of the olefinic gasoline range material to distillate boiling range material to provide a wide product mix. The compression costs are reduced because the $C_5^+$ rich stream 50 feeds the second catalytic reactor zone 60 as a liquid which may be pumped to the required pressure, whereas a $C_3/C_4$ type feed could require a compressor.

Figure 2:
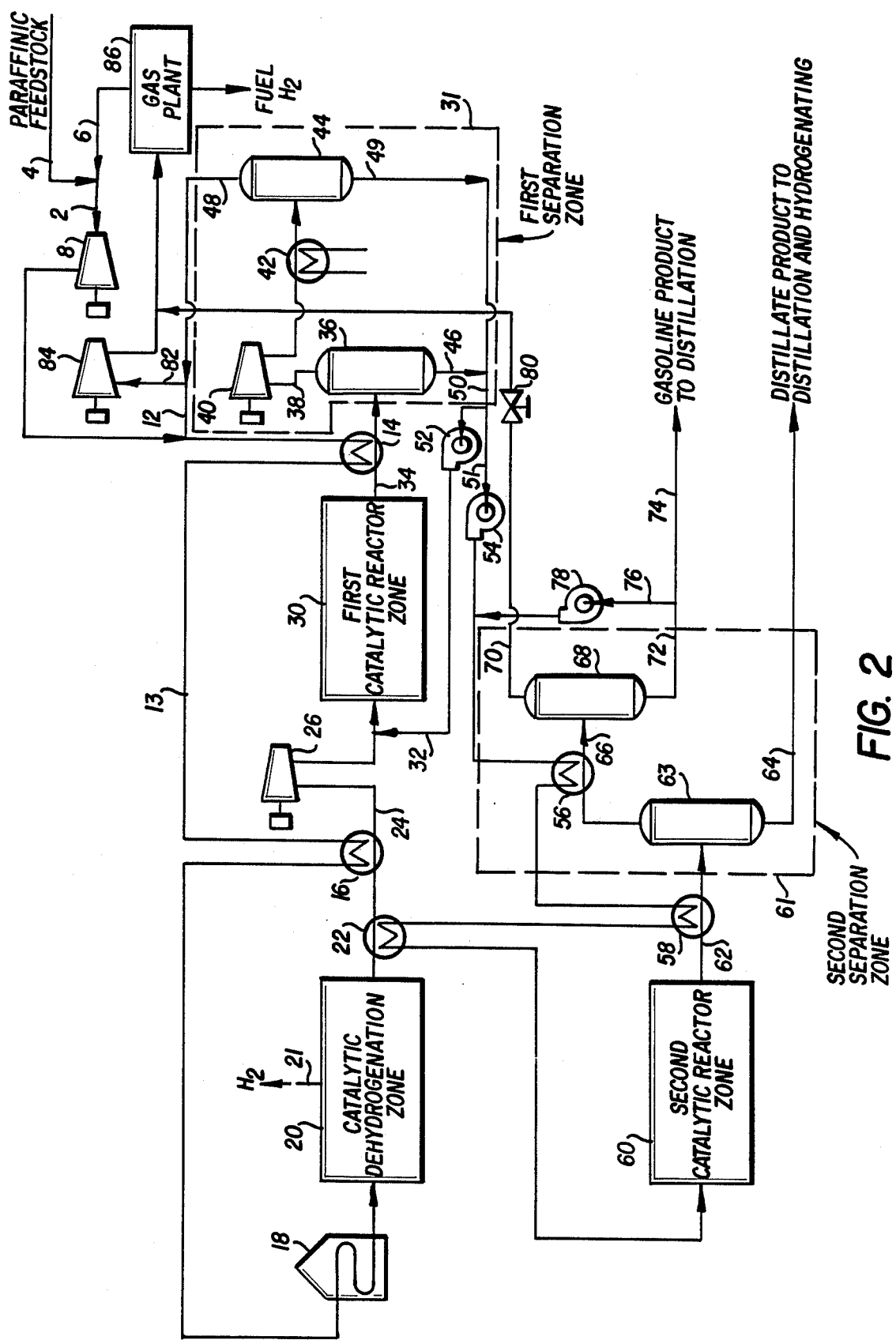
FIG. 2 is a schematic representation of a preferred embodiment of the apparatus of the invention which integrates dehydrogenation and a two-stage catalytic oligomerization of olefins.

FIG. 2 discloses the apparatus for implementing the preferred method of the invention in which dehydrogenation of paraffins is integrated with a process for converting olefins by catalytic oligomerization to produce heavier hydrocarbons of gasoline or distillate boiling range. Elements having correspondence to FIG. 1 are identified by the same reference number.

A first paraffins feedstock 4, from any conventional paraffins source, e.g., is combined with a second paraffins feedstock 6, from a gas plant 86 (the function of which is described below), to form a paraffinic feed stream 2. The paraffinic feed stream 2 then passes through a paraffinic feed stream turbo expander 8 to reduce the pressure of stream 2 to the pressure required for a catalytic dehydrogenation zone 20. Stream 2 then combines with recycled paraffinic feed stream 12 (discussed below) to form a combined paraffinic feed stream 13 which is heated in a first heat exchanger 14, a second heat exchanger 16, and a furnace 18 so that stream 13 exits the furnace 18 at a temperature greater than 1100° F. After heating, the combined paraffinic feed stream 13 enters a catalytic dehydrogenation zone 20 at conditions of low pressure and high temperature, which favor dehydrogenation of paraffins, comprising propane and/or butane, to an olefins rich effluent stream 24 comprising propylene and/or butylene, respectively, and an optional $H_2$ stream 21, depending upon the dehydrogenation method selected. The dehydrogenation method may be selected from a number of catalytic processes, such as Houdry Catofin or UOP Oleflex, or thermal dehydrogenation methods. Typical pressures in the catalytic dehydrogenation zone 20 range from 0.1 to 2 atmospheres, although U.S. Pat. No. 4,191,849 teaches pressures up to 500 psig can be used. Typical temperatures range from 1000°–1700° F. Typical conditions in thermal dehydrogenation range from 1400°–1700° F. and 0.1–2 atmospheres. The dehydrogenation method selected to be integrated with MOGD, determines whether there can be an $H_2$ stream 21. For example, the Houdry Catofin method could optionally produce an $H_2$ stream 21, whereas the UOP Oleflex process would produce an $H_2$ stream 21. The olefin rich effluent stream 24 is cooled in a third heat exchanger 22 and in second heat exchanger 16 to below 350° F. to prevent damage to a downstream effluent compressor 26. The cooled stream 24 is then compressed by the effluent compressor 26 and passes into a first catalytic reactor zone 30. In the first catalytic reactor zone 30, the olefin rich effluent stream 24 is reheated by a furnace or other means for heating to about 400° F.–800° F. and contacts a crystalline zeolite oligomerization catalyst at conditions of low pressure and high temperature, which favor conversion of olefins to form a first reactor effluent stream 34 rich in olefinic gasoline range hydrocarbons.

The first reactor effluent stream 34 is cooled by the first heat exchanger 14 to below 350° F., and then passes into a first separation zone 31 at a pressure of about 5–20 psig and temperature below 350° F. to prevent damage to a gas effluent compressor 84. The first separation zone 31 separates stream 34 into a $C_5{}^+$ rich stream 50 and a first $C_4{}^-$ rich stream 48. FIG. 2 shows the steps within zone 31, wherein the first reactor effluent stream 34 is flashed in a low pressure separator 36 to form a first vapor stream 38 which is rich in propylene or butylene, and a first liquid stream 46 which is rich in olefinic gasoline. The first vapor stream 38 is compressed by first vapor compressor 40, cooled by first vapor cooler 42, and flashed in a medium pressure separator operating at about 30–40 psig to separate the first vapor stream 38 into the first $C_4{}^-$ rich stream 48, and second liquid stream 49 which is rich in olefinic gasoline. The first $C_4{}^-$ rich stream is then divided into a gas effluent stream 82 and paraffins feed stream 12. Stream 82 passes through the gas effluent compressor 84 and passes to the gas plant 86, where stream 82 is separated into fuel gas, $H_2$ and the second paraffins feedstock 6. Feedstock 6 is combined with first paraffins feedstock 4 and recycled to the dehydrogenation zone 20. Stream 12 is combined with paraffinic feed stream 2 and recycled to the catalytic dehydrogenation zone 20. The first and second liquid streams 46,49 are combined to form the $C_5{}^+$ rich stream 50. Stream 50 is divided into a recycle stream 32 and a olefinic feedstock 51. Recycle stream 32 passes through recycle pump 52 and is recycled to the first catalytic reactor zone 30.

The olefinic feedstock 51 is pumped through an olefinic feedstock pump 54 and then heated by passing through a fourth heat exchanger 56, a fifth heat exchanger 58 and the third heat exchanger 22, and then enters the second catalytic reactor zone 60. The olefinic feedstock 51 is contacted with a crystalline zeolite oligomerization catalyst in the second catalytic reactor zone 60 at moderate pressure and high temperature under conditions favorable for production of a second reactor effluent stream 62 rich in distillate. In addition, prior to the fourth heat exchanger 56, the olefinic feedstock 51 may be combined with a gasoline recycle stream 76 to control temperature rise in the second catalytic reactor zone 60. Typically, cooled olefins and paraffins from downstream separation zones 31,61 are recycled back into reaction zones 30,60, respectively, to oligomerize the recycled olefins to gasoline and distillate products and provide a heat sink. The oligomerization of the olefins to distillate and gasoline is exothermic, so if it progresses without any measure taken to prevent the accumulation of heat, the reaction results in high temperatures and the production of undesired products.

The second reactor effluent stream 62 is cooled in fifth heat exchanger 58 and then passes into the second separation zone 61. The second separation zone 61 separates the second reactor effluent stream 62 into a second $C_4{}^-$ rich stream 70, a liquid gasoline stream 72 and a distillate product stream 64. In detail, shown in FIG. 2, in the second separation zone 61 stream 62 is passed into a high pressure, high temperature separator 63 to separate the stream 62 into a distillate product stream 64 and a second vapor stream 66. The second vapor stream 66 is cooled in the fourth heat exchanger 56 by heat exchange with the olefinic feedstock 51 and then flashed in a high pressure, moderate temperature separator 68 to form the liquid gasoline stream 72 and the second $C_4{}^-$ rich stream 70. The liquid gasoline stream 72 may be divided into a gasoline product stream 74, which is sent to downstream distillation, and a gasoline recycle stream 76 which is pumped through gasoline recycle pump 78 and combined with the olefinic feedstock 51. The second $C_4{}^-$ rich stream 70 may pass through a pressure let down valve 80 and then to the gas plant 86 to recover components, such as paraffins, fuel and $H_2$.

The oligomerization catalysts preferred for use in the reactors 30,60 include crystalline alumina silicate zeolites having a silica-to-alumina ratio of at least 12, a Constraint Index of about 1 to 12 and acid cracking activity of about 160–200. Representative of the ZSM-5 type zeolites are ZSM-5, ZSM-11, ZSM-12, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,859 for ZSM-38. The disclosures of these patents are incorporated herein by reference. A suitable shape selective catalyst for a fixed bed is a HZSM-5 zeolite with alumina binder in the form of cylindrical extrudates of about 1–5 millimeters. Other catalysts which may be used in one or more reactor stages include a variety of medium pore (5 to 9 Angstroms) siliceous materials, such as borosilicates, ferrosilicates and/or aluminosilicates, disclosed in U.S. Pats. Nos. 4,414,143 and 4,417,088, incorporated herein by reference.

The catalytic dehydrogenation zone 20 would operate at conditions depending upon which of a number of commercially available methods is selected. Typical catalytic dehydrogenation conditions range from about 0.1–2 atmospheres and 1000°–1700° F. Thermal dehydrogenation operates at similar conditions and could be used in lieu of catalytic dehydrogenation, however it is less selective for dehydrogenation of propane/butane than catalytic dehydrogenation so it produces more ethylene. U.S. Pat. No. 4,413,153 (Garwood et al) describes catalytic and thermal dehydrogenation in more detail. Table 1 shows sample yields from catalytic dehydrogenation of propane to propylene and butylene.

TABLE 1

| Sample Reactor Effluent From $C_3$ Catalytic Dehydrogenation Unit | | |
|---|---|---|
| | Feed | Effluent |
| $H_2$, wt % | | 2.2 |
| $CH_4$ | | 3.7 |
| $C_2H_4$ | 0.7 | 5.3 |
| $C_2H_6$ | .3 | 2.3 |
| $C_3H_6$ | | 39.0 |
| $C_3H_8$ | 98.0 | 46.2 |
| $C_4{}^+$ | 1.0 | 1.3 |

Figure 3:
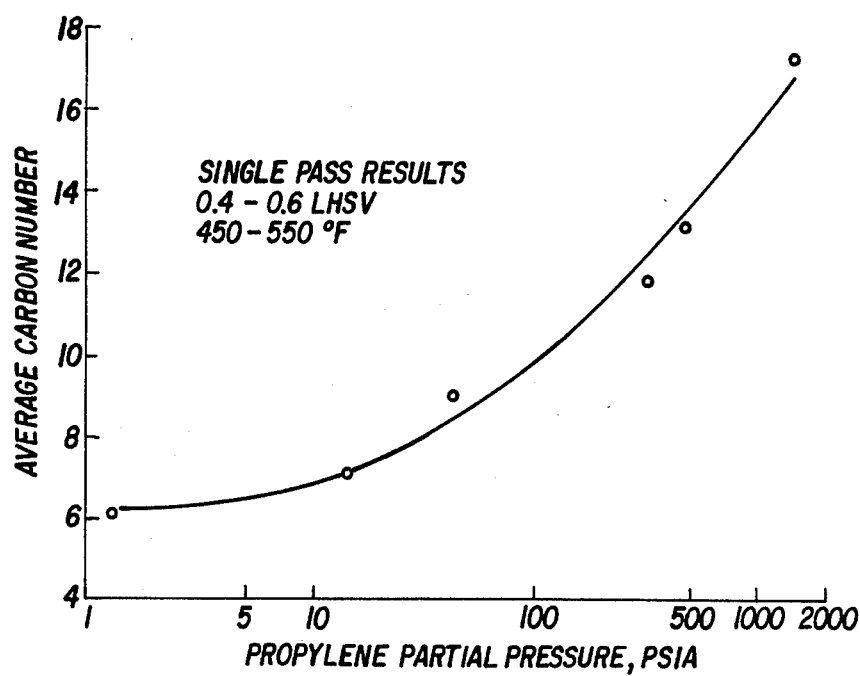
FIG. 3 is a plot of the effect of olefin pressure on the average carbon number of the product.

As shown by the curve on FIG. 3, the effect of olefin pressure on oligomerization product is significant because increased pressure results in a heavier, higher boiling range product. Therefore, the first catalytic reactor zone 30 would run at the lower pressure side of the curve, whereas the second catalytic reactor zone 60 would run at the higher pressure side of the curve.

A typical first catalytic reactor zone 30 would comprise a down flow reactor operating at pressures ranging from 10-1000 psia, preferably 10-40 psia, and from 400°-800° F., preferably 450°-600° F. Typical single pass conversions of $C_3/C_4$ olefins to olefinic gasoline would be from 70-95%, and preferably 80-95%. Space velocities would range from 0.2-4 WHSV (weight hourly space velocity), and preferably 0.5-1.5 WHSV. Table 2 presents an example of the yields from catalytic oligomerization in a first catalytic reactor zone 30 at low pressure for a propane and propylene feed converted to $C_5^+$ product, wherein said feed and product are representative of the olefin rich effluent stream 24 and the first reactor effluent stream 34, respectively, of FIG. 2. A representative process for conversion of olefins to gasoline is disclosed in U.S. Pat. No. 3,960,978 to Givens et al.

TABLE 2

Low Pressure MOGD
16.3 psig
Reactor 443° F. Inlet; 539° F. Outlet
0.5 WHSV
$C_3$ Partial Pressure at Reactor Inlet = 1.6 psia
14.8 Days on Stream
$C_3$ = Conversion 92.9% Single Pass
$N_2$ Diluent 18.2 moles/mole $C_3^=$

|  | Feed | Product (Converted Olefins) |
|---|---|---|
| $C_1$-$C_2$, wt % |  | .17 |
| $C_3$ | 38.0 | 1.33 |
| $C_3^=$ | 62.0 | — |
| i - $C_4$ |  | 2.21 |
| n - $C_4$ |  | .42 |
| $C_4^=$ |  | 23.73 |
| $C_5^+$ |  | 72.15 |

The general operating parameters for the second catalytic reactor zone 60 would be at pressures from 100-2000 psig at temperatures ranging from 350°-600° F., and space velocities of 0.2 to 10 WHSV, as disclosed in U.S. Pat. No. 4,211,640 to Garwood et al, which is incorporated herein by reference. Table 3 shows the yields from catalytic oligomerization of $C_5^+$ product to distillate product, wherein the feed and product are representative of streams 51,62, respectively, in FIG. 2.

TABLE 3

| High Pressure MOGD of $C_5^+$ Gasoline | | |
|---|---|---|
| 450° F. | | |
| 900 psig | | |
| 0.5 WHSV | | |
| ZSM-5 (70 $SiO_2/Al_2O_3$) | | |
|  | Feed* | Product |
| $C_1$-$C_4$, wt % |  | 4 |
| $C_5$- 330° F. | 90 | 19 |
| 330° F.+ | 10 | 77 |

*Low pressure MOGD gasoline 125° F.–350° F. boiling range

While specific embodiments of the method and apparatus aspects of the invention have been shown and described, it should be apparent that many modifications can be made thereto without departing from the spirit and scope of the invention. Accordingly, the invention is not limited by the foregoing description, but is only limited by the scope of the claims appended hereto.

We claim:

1. A method for producing heavier hydrocarbons of gasoline or distillate boiling range which comprises:
   (a) passing a paraffinic feed stream comprising at least one member selected from the group consisting of propane and butane into a dehydrogenation zone at conditions of pressure and temperature which favor conversion of paraffins to an olefin rich effluent stream comprising at least one member selected from the group consisting of propylene and butylene;
   (b) contacting the olefin rich effluent stream in a first catalytic reactor zone with a crystalline zeolite oligomerization catalyst at a pressure from 10-40 psia and temperature from 400°-800° F. to convert olefins to a first reactor effluent stream rich in olefinic gasoline range hydrocarbons;
   (c) separating the first reactor effluent stream in a first separation zone to form a $C_5^+$ rich stream comprising hydrocarbons having at least 5 carbon atoms and a first $C_4^-$ rich stream comprising hydrocarbons having at most 4 carbon atoms;
   (d) passing at least a first portion of the $C_5^+$ rich stream as an olefinic feedstock to a second catalytic reactor zone;
   (e) contacting the olefinic feedstock in the second catalytic reactor zone with a crystalline zeolite oligomerization catalyst at a pressure from 100-2000 psig and temperature from 350°-600° F. to produce a second reactor effluent stream which is rich in distillate; and
   (f) separating the second reactor effluent stream in a second separation zone to recover a second $C_4^-$ rich stream comprising hydrocarbons having at most 4 carbon atoms, a liquid gasoline stream, and a distillate product stream.

2. The method of claim 1, further comprising preheating the paraffinic feed stream prior to passing it into the dehydrogenation zone.

3. The method of claim 2, further comprising cooling and compressing the olefin rich effluent stream prior to passing it to the first catalytic reactor zone.

4. The method of claim 1, wherein the separation step in the first separation zone comprises the steps of:
   (a) flashing the first reactor effluent stream in a low pressure separator to separate the first reactor effluent stream into a first vapor stream rich in at least one of the group consisting of propylene and butylene, and a first liquid stream rich in olefinic gasoline;
   (b) flashing the first vapor stream in a medium pressure separator to separate the first vapor stream into the first $C_4^-$ rich stream and a second liquid stream; and
   (c) combining the first and second liquid streams to form the $C_5^+$ rich stream.

5. The method of claim 4, further comprising the steps of:
   dividing the first $C_4^-$ rich stream into a first portion and a second portion; and
   recycling the first portion to the dehydrogenation zone by combining the first portion with the paraffinic feed stream.

6. The method of claim 4, further comprising recycling a second portion of the $C_5^+$ rich stream to the first catalytic reactor zone.

7. The method of claim 1, wherein the separation step in the second separation zone comprises the steps of:

(a) passing the second reactor effluent stream into a high pressure, high temperature separator and separating the stream into the distillate product stream and a second vapor stream; and (b) flashing the second vapor stream in a high pressure and moderate temperature separator to form the liquid gasoline stream and the second $C_4^-$ rich stream.

8. The method of claim 1, further comprising dividing the liquid gasoline stream into a gasoline product stream and a gasoline recycle stream, the latter being combined with the olefinic feedstock and recycled to the second catalytic reactor zone.

9. The method of claim 1, further comprising expanding the paraffinic feed stream prior to its passing into the dehydrogenation zone.

10. The method of claim 2, wherein preheating of the paraffinic feed stream comprises the steps of:

(a) heating the paraffinic feed stream by heat exchange with the first reactor effluent stream;

(b) heating the paraffinic feed stream by heat exchange with the olefin rich effluent stream from the dehydrogenation zone; and (c) heating the paraffinic feed stream in a furnace upstream of the dehydrogenation zone.

11. The method of claim 7, further comprising the step of heating the olefinic feedstock prior to passing it to the second catalytic reactor zone.

12. The method of claim 11, wherein the heating of the olefinic feedstock comprises the steps of:

(a) heating the olefinic feedstock by heat exchange with the vapor from the high temperature, high pressure separation;

(b) heating the olefinic feedstock by heat exchange with the second reactor effluent stream; and (c) heating the olefinic feedstock by heat exchange with the olefin rich effluent stream.

13. The method of claim 1, wherein the first and second catalyst reactor zones comprise a fixed bed downflow pressurized reactor having a porous bed of zeolite catalyst.

14. The method of claim 1, wherein the first catalyst reactor zone is maintained a space velocity of 0.2–4 WHSV.

15. The method of claim 1, wherein the second catalytic reactor zone is maintained at a space velocity ranging from 0.2–10 WHSV.

16. The method of claim 1, wherein the first catalytic reactor zone contains at least one catalyst from the group consisting of ZSM-5, ZSM-11, ZSM-12, ZSM-23, ZSM-35 and ZSM-38.

17. The method of claim 1, wherein the first and second catalytic reactor zones contain at least one catalyst from the group consisting of ZSM-5, ZSM-11, ZSM-12, ZSM-23, ZSM-35 and ZSM-38.

18. The method of claim 1, wherein the dehydrogenation zone is a catalytic dehydrogenation zone.

19. The method of claim 1, wherein said dehydrogenation zone is a thermal dehydrogenation zone.

20. The method of claim 1, wherein the olefinic feedstock is pumped into the second catalytic reactor zone.

* * * * *